United States Patent
Desecki et al.

[11] Patent Number: 5,947,932
[45] Date of Patent: Sep. 7, 1999

[54] CLOSED SYSTEM BLOOD SAMPLING DEVICE

[75] Inventors: Vincent C. Desecki, Ingleside; Glennie Browne, Buffalo Grove, both of Ill.

[73] Assignee: Baxter International Inc., Deerfield, Ill.

[21] Appl. No.: 08/886,168

[22] Filed: Jun. 30, 1997

Related U.S. Application Data

[63] Continuation of application No. 08/777,729, Dec. 20, 1996, abandoned, which is a continuation of application No. 08/296,207, Aug. 25, 1994, abandoned.

[51] Int. Cl.$^6$ .................................................. A61M 5/00
[52] U.S. Cl. ............................................ 604/190; 604/256
[58] Field of Search ........................... 604/35, 122, 125, 604/126, 190, 199, 256, 258, 283, 284, 405, 406, 115; 128/912

[56] References Cited

U.S. PATENT DOCUMENTS

| | | | |
|---|---|---|---|
| 2,455,645 | 12/1948 | Barton | 604/405 |
| 3,978,846 | 9/1976 | Bailey | 604/125 X |
| 4,215,702 | 8/1980 | Ayer . | |
| 4,430,081 | 2/1984 | Timmermans | 604/256 |
| 4,459,139 | 7/1984 | Von Reis et al. | 604/126 X |
| 4,531,937 | 7/1985 | Yates | 604/122 X |
| 4,723,955 | 2/1988 | Vaillancourt | 604/405 |
| 4,843,017 | 6/1989 | Oberhardt et al. | 128/762 X |
| 4,900,308 | 2/1990 | Verkaart | 604/126 |
| 4,911,705 | 3/1990 | Heinzerling et al. | 604/122 X |
| 5,041,106 | 8/1991 | Noji et al. | 604/126 X |
| 5,207,656 | 5/1993 | Kranys | 604/256 |
| 5,267,966 | 12/1993 | Paul | 604/256 X |
| 5,300,034 | 4/1994 | Behnke et al. . | |
| 5,300,084 | 4/1994 | Johnson | 604/264 |

FOREIGN PATENT DOCUMENTS

| | | |
|---|---|---|
| 0000831 | 8/1978 | European Pat. Off. . |
| 0301913 | 8/1988 | European Pat. Off. . |
| 0376168 | 12/1989 | European Pat. Off. . |

*Primary Examiner*—Wynn Wood Coggins
*Assistant Examiner*—Sharon Finkel
*Attorney, Agent, or Firm*—Jeffrey C. Nichols; Mark J. Buonaiuto; Francis C. Kowalik

[57] ABSTRACT

The invention comprises a closed system blood sampling device comprising a bifurcated capillary tube which has a first branch having a cannula shaped end for withdrawing and conveying blood to a communicating blood collection zone. The blood collection zone is for storing a quantity of withdrawn blood. It also feeds an initial fraction of withdrawn blood to a communicating blood disposal chamber which has an air permeable liquid sealed end. The second branch of the bifurcated capillary tube is connected to and is in fluid communication with the blood collection zone. It terminates in an opening adapted to receive a blood withdrawal device. Also disclosed is a method of sampling blood from a patient having an artery fitted with a venipuncture device which is attached to an injection site which contains the closed blood sampling device described.

12 Claims, 2 Drawing Sheets

CLOSED SYSTEM BLOOD SAMPLING DEVICE

This is a continuation of application Ser. No. 8/777,729 filed Dec. 20, 1996, abandoned which is a continuation of application Ser. No. 8/296,207, filed Aug. 25, 1994, abandoned.

FIELD OF THE INVENTION

The invention relates to closed system blood sampling devices.

BACKGROUND OF THE INVENTION

Arterial blood gas sampling is a standard procedure often used to help assess respiratory function in the critically ill. In some cases, samples can be drawn as many as 20 times a day. For the typical neonatal patient weighing 1000 grams and having approximately 85 cc of total body fluid capacity, the volume of blood samples becomes a critical factor.

A technique called the 3 drop method is gaining substantial clinical acceptance in neonatal units across the country. This method calls for inserting a blunt hypodermic needle as far as possible into a standard sleeve stoppered T-Connector. Three drops of blood estimated to be approximately 0.06 cc are allowed to drip onto a gauge pad, thereby clearing the cannula of heparinized or non-circulating blood while providing a fresh arterial sample to the surface. 3 more drops are then collected in a micro container followed by cannula withdrawal. Blood cannula contents within the cannula lumen and the previously collected micro container sample are then aspirated into a tuberculin type syringe for transport to the blood lab for testing. A flush of the T-Connector to eliminate residual blood then ensues. This procedure provides the ability to withdraw a controlled blood volume; 0.06 cc as necessary discard and 0.12 cc to perhaps 0.20 cc for actual blood gas testing.

Several opportunities for procedural improvement exist. One challenge is the open environment method of collection which could foster blood contamination and/or the spread of infectious diseases. Secondarily, the collection process in regard to volume accuracy is difficult to control and highly sensitive to variations in clinician technique, catheter positioning and arterial pressure. If a device can be designed for closed system collection which could also insure consistency of sample volume time after time, treatment of neonatal patients where blood volume levels are critical, accuracy improvements could be a major clinical benefit.

THE DRAWINGS

In the drawings, like parts have like numbers.

THE INVENTION

The invention is a closed system blood sampling device comprising a bifurcated capillary tube which has a first branch having a cannula shaped end for withdrawing and conveying blood to a communicating blood collection zone. The blood collection zone is for storing a quantity of withdrawn blood. It also feeds an initial fraction of withdrawn blood to a communicating blood disposal chamber which has an air permeable liquid sealed end.

The second branch of the bifurcated capillary tube is connected to and is in fluid communication with the blood collection zone. It terminates in an opening adapted to receive a blood withdrawal device.

In preferred embodiments the closed system blood sampling device the cannula shaped end is blunt, the blood disposal chamber has its end fitted with a cap containing an air permeable hydrophobic membrane, and the blood disposal chamber contains a porous blood adsorbent. The second branch has an interior angle not greater than 90 degrees and preferably the interior angle is 60 degrees. It is also desirable that the cannula shaped end be tapered so that it snugly fits into the preferred injection sites more fully described hereafter.

Preferably, the closed system blood sampling device is removed from the injection site before the blood sample is withdrawn therefrom by means such as a tuberculum syringe or aspirated directly into a blood gas analyzer.

While the closed blood sampling device is particularly suited for obtaining neonatal blood samples it is readily adapted to obtain samples from a variety of patient types.

DETAILED DESCRIPTION OF THE INVENTION

Figure 1:
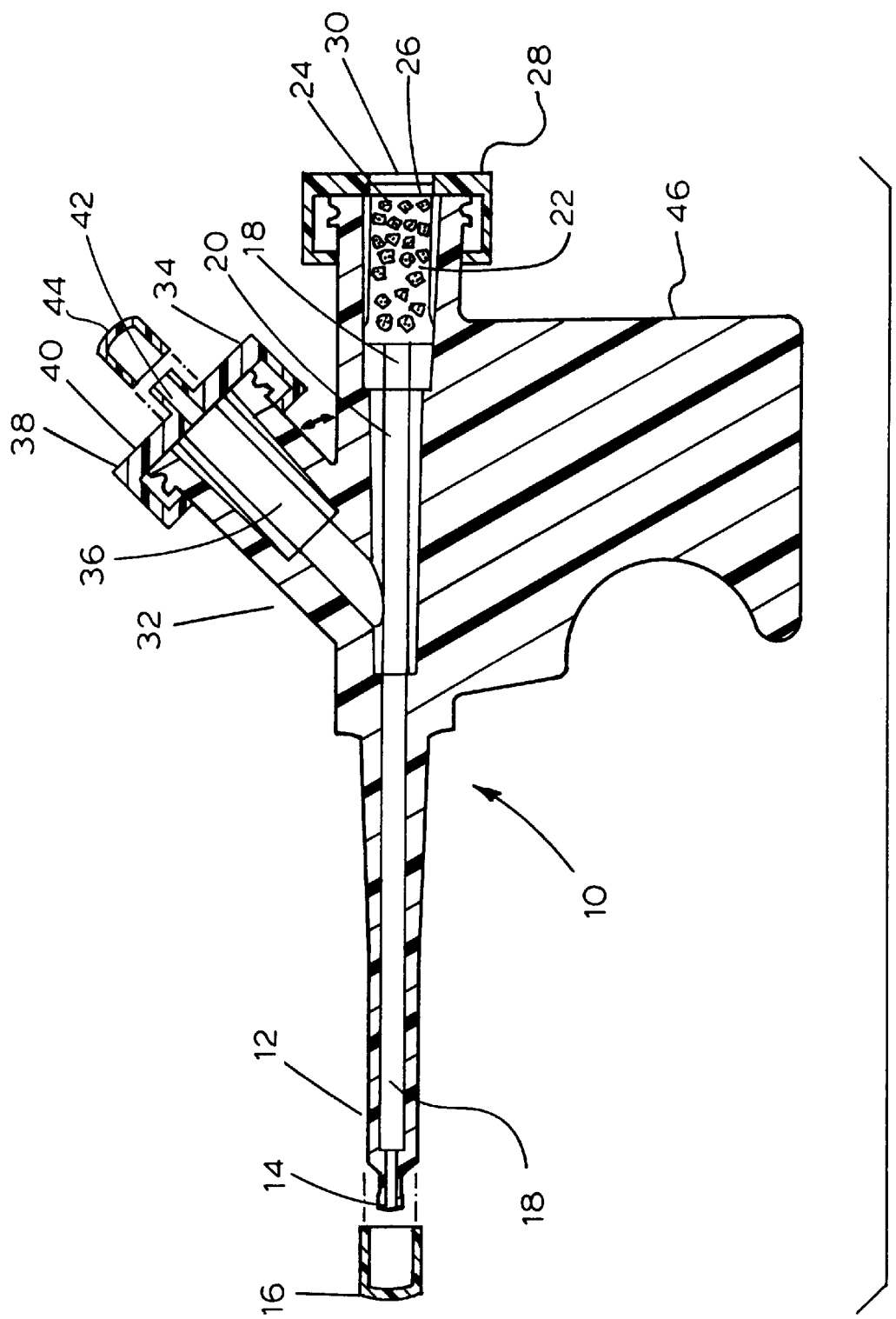
FIG. 1 is a horizontal cut away side view showing the closed system blood sampling device of the invention.

In FIG. 1 the closed system blood sampling device is designated generally by the numeral 10. It is preferably constructed of a clear chemically inert non-toxic plastic such as polycarbonate. It comprises a blood withdrawal cannula shaped end 12. The cannula tip 14 is blunt and necked down to prevent injection site from blood flash back during arterial sampling. To maintain sterility the cannula tip is fitted with a removable cap 16 which is removed just before the blood sampling device is to be used.

FIG. 1 shows the cannula shaped end 12 to be tapered. This particular configuration was selected so that the cannula may engage and generally mate with a particular injection site, the details of which will be more fully described hereafter. The interior bore 18 of the cannula shaped end is dimensioned to allow withdrawn blood to move along the bore by means of capillary action driven by normally positive arterial blood pressure.

The interior capillary bore 18 connects with and continues into a larger outer diameter lumen 20. The continuous bore 18 of the cannula 12 and the lumen 20 comprise a blood collection zone. Bore 18 as it exits the lumen 20 empties into blood disposal chamber 22. In a preferred embodiment of the invention, blood disposal chamber 22 contains a blood retaining means such as adsorbing material 24 which may be rayon or cellulosic wadding. The open end 26 of the blood disposal chamber 22 is closed with a cap 28 that has its top fitted with a liquid tight, air permeable hydrophobic membrane 30 which allows air to be evacuated from the blood sampling device 10 of the invention. A suitable membrane material is sheet polytetrafloroethylene having a thickness of about 0.8 microns.

Fitted to the lumen 20, and in fluid communication therewith, is the second branch or port 32. It is positioned so as to have an interior angle 34 not exceeding 90 degrees. The interior angle is preferably about 60 degrees. The bore 36 connects with and corresponds in dimension with bore 18. Port 32 terminates and is sealed by adapter cap 38 whose top 40 is fitted with a capillary luer 42. The capillary luer is protected from contamination by means of protective cap 44 which is removed just prior to blood being withdrawn from the closed blood sampling device. The port 32 and its bore 36 form a part of the blood collection zone previously described. For convenience of use, the closed blood sampling device is fitted with pistol grip handle 46.

The blood collection zone has a larger liquid capacity than the liquid capacity of the blood disposal chamber. If the closed blood sampling device described were to be used in neonatal blood sampling, the liquid capacity of the blood collection zone might be 0.12 cc and the liquid capacity of the blood disposal chamber 22 would be about 0.06 cc.

Figure 2:
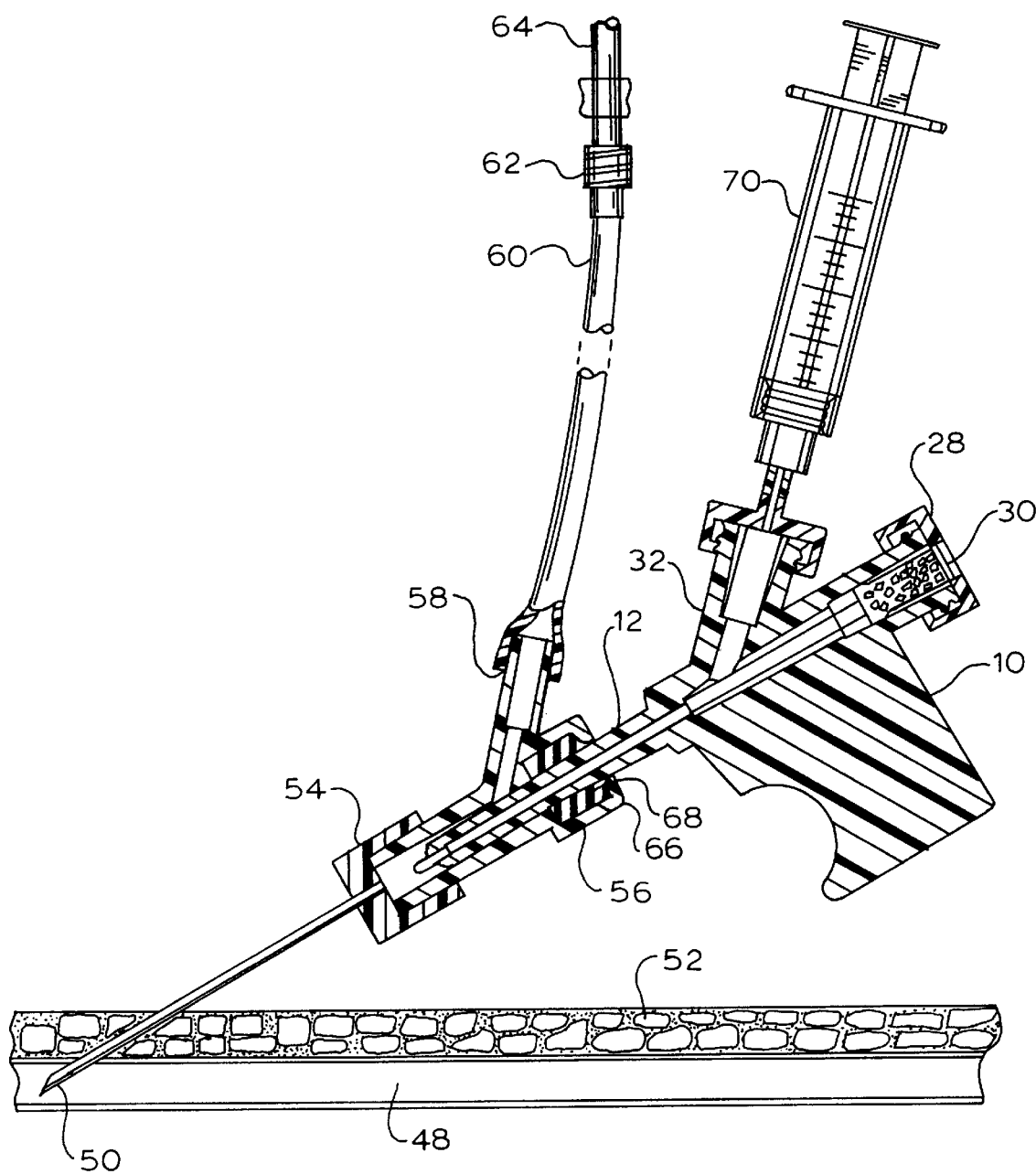
FIG. 2 is a vertical, partial schematic view showing the closed system blood sampling device connected to an injection site which, in turn, is fitted into a venipuncture device used to withdraw arterial blood.

The use of the closed blood sampling device of the invention to withdraw and sample blood is illustrated in FIG. 2 which shows artery 48 in communication with a venipuncture device 50 which was inserted through subcutaneous tissue 52. The neck 54 of the venipuncture device 50 is adapted to receive an injection site 56. While conventional injection sites may be used as such or adapted to be used in the practice of the invention, it is preferred that the injection site be of the type having a resilient resealable septum which is preferably pre-slit. An injection site of this type is available from Baxter Healthcare Corporation and is a Neonatal T-Connector Luer sold under the brand name, InterLink, a registered trademark of Baxter Healthcare Corporation.

Such pre-slit, resilient, resealable injection sites and their method of fabrication are described in U.S. Pat. No. 5,188,620 the disclosure of which is incorporated herein by reference. The pre-slit resilient resealable injection sites described in this patent are designed to receive blunt cannulas. Another injection site related to the injection sites detailed in U.S. Pat. No. 5,188,620 is described in U.S. Pat. No. 5,300,034. This patent also details numerous publications and references which describe the preferred injection sites used in the practice of this invention. This patent and the publications listed therein also are incorporated herein by reference.

The injection site 56 is fitted with T-connector 58 which, in turn, is fitted with microbore tubing which, through female luer 62, is connected to IV line 64. The distal end 64 of the injection site 56 is connected to the neck 54 of the venipuncture device 50. The proximal end 66 of the injection site 56 is fitted with a pre-slit resilient resealing septum 68 adapted to receive the blood withdrawal cannula 12 which is dimensioned to fit snugly into the injection site. Inserted into the second branch or port 32 is a conventional syringe 70, such as a tuberculum blood draw syringe, or an arterial blood gas loss of resistance syringe.

The device's cannula 12 would be inserted through the septum 68 of the injection site 56 and positioned so that the tip 14 of the cannula 12 was fully inserted into the injection site adjacent to the venipuncture device. In doing so, the residual volume of the actual T-Housing would be eliminated as a measurable factor in blood draw volume. Arterial pressure would cause blood flow to enter and flow up the device via capillary action. As blood moved up the hydrophobic membrane 30 of the device, air would escape via the upstream hydrophobic membrane 30. Original blood first present in the catheter would be pushed beyond the luer bifurcation for retention in the device and eventual disposal. The device would be withdrawn from the T-Connector as soon as visual confirmation of the blood filled lumen was made. The vented removal cap 44 would be removed from the bifurcated luer 42 and replaced by the syringe 70 which would be aspirated to remove the arterial blood sample. Residual blood volume upstream of the bifurcation would remain in the device for subsequent disposal.

We claim:

1. A closed system sampling device for sampling blood through an injection site, said device comprising:

a rigid cannula member extending forward to form a forward end of said device, said cannula member being configured to have a blunt forward tip which initially contacts the injection site, said cannula member forming a bore which extends rearward from said forward tip;

a lumen formed within said device, said lumen being rearward of said cannula, said bore extending rearward from said tip and opening into said lumen;

a second branch defining a port in liquid communication with and opening into said lumen;

a disposal chamber formed within said device and connected to said lumen, said chamber, lumen and bore arranged so that blood flows rearward from said bore into said lumen and then into said chamber, said chamber having a first end;

a liquid tight member disposed at said first end of said disposal chamber, said liquid tight member being air permeable and liquid tight, one side of the liquid tight member being visible; and an absorbent medium disposed within said disposal chamber between said liquid tight member and said lumen and opened to said lumen so that the blood flows into the absorbent medium.

2. The system of claim 1 wherein said liquid sealing member includes a thin hydrophobic membrane covering said first end.

3. The system of claim 1 wherein said absorbent medium includes a cellulosic wadding.

4. The system of claim 1 wherein said port within said second branch is sealed with a cap having a capillary luer connection fitting.

5. The system of claim 1 wherein said second branch is angled relative to said bore of said cannula.

6. The system of claim 1 wherein said bore, said lumen and said disposal chamber are generally elongated and aligned with each other.

7. The system of claim 1 wherein said bore opens into a forward end of said lumen and said disposal chamber opens into a rearward end of said lumen.

8. A closed system sampling device for sampling blood through an injection site, said device comprising:

a rigid cannula member extending forward to form a forward end of said device, said cannula member being configured to have a blunt forward tip which initially contacts the injection site, said cannula member forming a bore which extends rearward from said forward tip;

a lumen formed within said device, said lumen being rearward of said cannula, said bore extending rearward from said tip and opening into said lumen;

a second branch defining a port in liquid communication with said lumen and opening into said lumen;

a disposal chamber formed within said device and connected to said lumen, said chamber, lumen and bore arranged so that fluid flows rearward from said bore into said lumen and then into said chamber, said chamber having a first end;

a liquid tight member disposed at said first end of said disposal chamber, one side of the liquid tight member being visible; and an adsorbent medium disposed within said disposal chamber between said liquid tight member and said lumen and opened to said lumen so that the blood flows into the absorbent medium.

9. A closed system sampling device for sampling blood through an injection site, said device comprising:
- a rigid cannula member extending forward to form a forward end of said device, said cannula member being configured to have a blunt forward tip, said cannula member forming a bore which extends rearward from said forward tip;
- a completely hollow lumen formed within said device, said lumen being rearward of said cannula, said bore extending rearward from said tip and opening into said lumen;
- a second branch defining a port in liquid communication with said lumen and opening into said lumen;
- a disposal chamber formed within said device and connected to said lumen, said chamber, lumen and bore arranged so that fluid flows rearward from said bore into said lumen and then into said chamber, said chamber having a first end;
- a liquid tight member disposed at said first end of said disposal chamber; and
- an absorbent medium disposed within said disposal chamber and between said lumen and said liquid tight member so that blood flows from said lumen into said absorbent medium.

10. A closed system sampling device for sampling blood through an injection site, said device comprising;
- a cannula member entirely formed of a rigid material and extending forward to form a forward end of said device, said cannula member being configured to have a blunt forward tip which initially contacts a injection site, said cannula member forming a bore which extends rearward from said forward tip;
- a lumen formed within said device, said lumen being rearward of said cannula, said bore extending rearward from said tip and opening into said lumen;
- a second branch defining a port in liquid communication with said lumen and opening into said lumen;
- a disposal chamber formed within said device and connected to said lumen, said chamber, lumen and bore arranged so that fluid flows rearward from said bore into said lumen and then into said chamber, said chamber having a first end;
- an absorbent medium disposed within said disposal chamber and exposed to said lumen so as to allow for blood to flow from said lumen into said medium; and
- a hydrophobic membrane disposed at said first end of said disposal chamber.

11. A closed system sampling device for sampling blood through an injection site, said device comprising:
- a rigid cannula member extending forward to form a forward end of said device, said cannula member being configured to have a blunt tip, said cannula member forming a bore which extends rearward from said forward tip;
- a lumen formed within said device, said lumen being rearward of said cannula;
- a second branch defining a port opening into said lumen;
- a disposal chamber formed within said device and connected to said lumen, said chamber having a first end, said lumen, said disposal chamber and said bore being configured so that blood flowing up said bore flows into said lumen prior to flowing into said disposal chamber;
- a liquid tight member disposed at said first end of said disposal chamber; and
- an absorbent medium formed of a material differing from said sealing member and disposed within said disposal chamber said absorbent medium opened to said lumen so that blood flows from said lumen into said absorbent medium.

12. A method for penetrating an injection site and sampling blood with a blood sampling device comprising:
- penetrating the injection site with a rigid cannula member extending forward to form a forward end of said device, said cannula member being configured to have a blunt tip, said cannula member forming a bore which extends rearward from said forward tip, said device forming, a lumen rearward of said cannula, a second branch defining a port in liquid communication with said lumen, and a disposal chamber connected to said lumen, said chamber having a first end, said lumen, said disposal chamber and said bore being configured so that blood flowing up said bore flows into said lumen prior to flowing into said disposal chamber, said device also including a liquid tight member disposed at said first end of said disposal chamber and an absorbent medium disposed within said disposal chamber;
- flowing initial blood up the bore through the lumen and to the chamber and absorbing the blood into an absorbent material disposed within the chamber;
- visually confirming that the lumen is filled with blood; and
- after visual confirmation, removing blood from within the lumen through the port for sampling.

* * * * *